United States Patent [19]
Humphries

[11] Patent Number: 5,258,299
[45] Date of Patent: * Nov. 2, 1993

[54] AVIAN IMMUNOGLOBULIN-PRODUCING CELL LINES

[75] Inventor: Eric H. Humphries, Morgantown, W. Va.

[73] Assignee: Board of Regents, The University of Texas System, Austin, Tex.

[*] Notice: The portion of the term of this patent subsequent to Jul. 2, 2008 has been disclaimed.

[21] Appl. No.: 640,481

[22] Filed: Jan. 14, 1991

Related U.S. Application Data

[63] Continuation-in-part of Ser. No. 289,599, Dec. 21, 1988, Pat. No.

[51] Int. Cl.$^5$ .................. C12N 5/00; C12N 15/00; A61K 39/00
[52] U.S. Cl. .................. 435/240.2; 435/240.1; 435/172.3; 435/317.1; 435/948; 424/88; 935/111
[58] Field of Search ............ 435/240.2, 240.27, 240.1, 435/240.26, 172.2, 172.3, 317.1, 948; 935/57, 111

[56] References Cited

U.S. PATENT DOCUMENTS 5,028,540 7/1991 Humphries .................. 435/240.2
5,049,502 9/1991 Humphries .................. 435/240.2

FOREIGN PATENT DOCUMENTS

A0090898 12/1982 European Pat. Off. .

OTHER PUBLICATIONS

Reference Purchase et al., A New Group of Oncogenic Viruses: Reticuloendotheliosis, Chick Syncytial, Duck Infectious Anemia, and Spleen Necrosis Viruses, Journal of the National Cancer Institute, vol. 51, Aug. 1973, pp. 489-497.
Reference Shibuya et al., Morphological, Immunological, and Biochemical Analyses of Chicken Spleen Cells Transformed in vitro by Reticuloendotheliosis Virus Strain T, Cancer Research, vol. 42, Jul. 1982, pp. 2722-2728.
Reference Wong et al., Avian Reticuloendotheliosis Virus Contains a New Class of Oncogene of Turkey Origin, Virology, vol. 111, Jan. 1981, pp. 289-293.
Reference Chen et al., Characterization of Reticuloendotheliosis Virus Strain T DNA and Isolation of a Novel Variant of Reticuloendotheliosis Virus Strain T by Molecular Cloning, Journal of Virology, vol. 40, No. 3, Dec. 1981, pp. 800-811.
Reference Temin, H. M. et al., Replication of Reticuloendotheliosis Viruses in Cell Culture: Acute Infection, Journal of Virology, vol. 13, No. 2, Feb. 1974, pp. 291-297.
Reference Witter, R. L. et al., Tolerance, Viral Shedding, and Neoplasia in Chickens Infected with NonDefective Reticuloendotheliosis Viruses, Avian Diseases, vol. 25, No. 2, Aug. 1980, pp. 374-394.
Reference Witter, R. L. et al., Lymphomas Resembling Lymphoid Leukosis In Chickens Inoculated With Reticuloendotheliosis Virus, Int. J. Cancer, vol. 23, Jan. 1979, pp. 673-678.

(List continued on next page.)

Primary Examiner—Jasemine C. Chambers
Attorney, Agent, or Firm—Arnold, White & Durkee

[57] ABSTRACT

The present invention relates to a method of preparing efficiently producing antibody avian cell clones. The method generally involves infecting a B-lymphocyte population with a v-rel gene using transfection or infection with a reticuloendotheliosis virus or reticuloendotheliosis virus and helper virus. The transformed B-cells are first isolated from the spleen or bursa, and then proliferated either in vivo in a second bird or in vitro in a liquid medium. Cell clones producing IgM, IgG or IgA may be selected. Prior immunization of the first bird with a desired antigen can be used to stimulate immunoglobulin producing cells.

12 Claims, 8 Drawing Sheets

OTHER PUBLICATIONS

Reference Noori-Daloii et al., Specific integration of REV proviruses in avian bursal lymphomas, Nature, vol. 294, Dec. 1981, pp. 574–576.

Reference Swift et al., Insertional Activation of c-myc by Reticuloendotheliosis Virus in Chicken B Lymphoma: Nonrandom Distribution and Orientation of the Proviruses, Journal of Virology, vol. 54, No. 3, Jun. 1985, pp. 869–872.

Reference Bueg et al., Hematopoietic Cells Transformed in vitro by REVT Avian Reticuloendotheliosis Virus Express Characteristics of Very Immature Lymphoid Cells, Virology, vol. 115, 1981, pp. 295–309.

Reference Lewis et al., Avian Reticuloendotheliosis Virus: Identification of the Hematopoietic Target Cell for Transformation, Cell., vol. 25, Aug. 1981, pp. 421–431.

Reference Zhang et al., Rearrangement and Diversification of Immunoglobulin Light-Chain Genes in Lymphoid Cells Transformed by Reticuloendotheliosis Virus, vol. 9, Nov., 1989, pp. 4970–4976.

Reference Siden et al., Immunoglobulin Synthesis by Lymphoid Cells Transformed in vitro by Abelson Murine Leukmia Virus, Cell, vol. 16, Feb. 1979, pp. 389–396.

Reference Franklin et al., Isolation and Characterization of Reticuloendotheliosis Virus Transformed Bone Marrow Cells, Intervirology, vol. 3, 1974, pp. 342–352.

Reference Hoelzer, J. D., et al., Transformation by Reticuloendotheliosis Virus: Development of a Focus Assay and Isolation of a Nontransforming Virus, Virology, vol. 93, 1979, pp. 20–30.

Reference Eskola et al., Effect of in Ovo Treatment with Cyclophosphamide on Lymphoid System in Chicken, Cellular Immunology, vol. 13, Feb. 1974, pp. 459–471.

Reference Baba et al., Avian Leukosis Virus Infection: Analysis of Viremia and DNA Integration in Susceptible and Resistant Chicken Lines, Journal of Virology, vol. 51, No. 1, pp. 123–130.

Reference Hahn et al., Lymphoproliferative Diseases of the Fowl: JM-V leukemic lymphoblasts in cell culture: brief communication, J. Natl. Canc. Inst., vol. No. 59, 1977, p. 267.

Reference Waite et al., RNA Directed DNA Polymerase Activity of Reticuloendotheliosis Virus: Characterization of the Endogenous and Exogenous Reactions, Journal of Virology, vol. 16, No. 4, Oct. 1975, pp. 872–879.

Reference Cui et al., Monoclonal Antibodies Against Avian Reticuloendotheliosis Virus: Identification of Strain Specific and Strain Common Epitopes, Journal of Immunology, vol. 136, No. 11, Jun. 1986, pp. 4237–4242.

Reference Baba et al., Formation of a transformed follicle is necessary but not sufficient for development of an avian leukosis virus induced lymphoma, Proc. Natl. Acad. Sci., vol. 82, Jan. 1985, pp. 213–216.

Reference Humphries et al., Characterization of Endogenous Viral Loci in Five Lanes of White Leghorn Chickens, Virology, vol. 135, Feb. 1984, pp. 125–138.

Reference Wilhelmsen et al., Structure and Dimorphism of c-rel (turkey), the Cellular Homolog to the Oncogene of Reticuloendotheliosis Virus Strain T, Journal of Virology, vol. 49, No. 2, Feb. 1984, pp. 521–529.

Reference Taylor et al., Chronologic Study of the T-Virus in Chicks., II. Development of Hematologic Changes, Avian Diseases, vol. 17, Jun. 1973, pp. 794–802.

Reference DeBoer et al., Horizontal Transmission of lymphoid leukosis virus Influence of age, material antibodies and degree of contact exposure, Avain Path., 1981, vol. 10, p. 343.

Reference Crittenden et al., Influence of Endogenous viral (ev) Gene Expression and Strain of Exogenous Avian Leukosis Virus (ALV) on Mortality and ALV Infection and Shedding in Chickens, Avian Diseases, vol. 28, No. 4, May 1984, pp. 1037–1056.

Reference Rup et al., Immunosuppression Induced By Avian Reticuloendotheliosis Virus: Mechanism of Induction Of The Suppressor Cell, The Journal of Immunology, vol. 123, No. 3, Sep. 1979, pp. 1362–1370.

Reference Witter et al., Depression of Vaccinal Immunity to Marek's Disease by Infection with Reticuloendotheliosis Virus, Infection and Immunity, vol. 26, No. 1, Oct. 1979, pp. 90–98.

Reference Rice et al., Genome of Reticuloendotheliosis Virus: Characterization by Use of Cloned Proviral DNA, Journal of Virology, Apr. 1982, vol. 42, No. 1, pp. 237–252.

(List continued on next page.)

OTHER PUBLICATIONS

Reference Chen et al., Structure and Expression of c-rel, the Cellular Homolog to the Oncogene of Reticuloendotheliosis Virus Strain T, Journal of Virology, vol. 45, No. 1, Jan. 1983, pp. 104–113.

Reference Mussman, H. C. et al., Pathogenesis of Reticuloendothelial Virus Disease in Chicks-An Acute Runting Syndrome, Avian Dis., vol. 15, Dec. 1970, pp. 483–502.

Reference Olson, L. D., Histopathologic and Hematologic Changes In Moribund Stages of Chicks Infected with T-Virus, Am. J. Vet. Res., vol. 28, No. 126, Sep. 1967, pp. 15011507.

Reference Theilen et al., Biological Studies With RE Virus (Strain T) That Induces Reticuloendotheliosis in Turkeys, Chickens, and Japanese Quail, J. Natl. Cancer Inst., vol. 37, No. 6, Dec. 1966, pp. 731–739.

Reference Keller et al., Isolation and Development of a Reticuloendotheliosis Virus Transformed Lymphoblastoid Cell Line from Chicken Spleen, Infection and Immunity, vol. 25, No. 2, Aug. 1979, pp. 694–701.

Reference Rosenberg et al., The Effect of Helper Virus On Abelson Virus Induced Transformation of Lymphoid Cells, J. Exp. Med., vol. 147, 1978, pp. 1126–1141.

Reference Ruscetti et al., Biological and Biochemical Differences between Variants of Spleen Focus Forming Virus Can Be Localized to a Region Containing The 3' End of the Envelope Gene, Journal of Virology, vol. 56, No. 3, Dec. 1985, pp. 717–722.

Reference Rup et al., Helper Viruses Associated With Avian Acute Leukemia Viruses Inhbit the Cellular Immune Response, Virology, vol. 116, 1982, pp. 61–71.

Reference Baba et al., Selective Integration of Avian Leukosis Virus in Different Hematopoietic Tissues, Virology, vol. 155, 1986, pp. 557–566.

Reference Cianciolo et al., Inhibition of Lymphocyte Proliferation by a Synthetic Peptide Homologous to Retroviral Envelope Proteins, Science, vol. 230, Oct. 1985, pp. 453–456.

Reference Sonigo et al., Nucleotide Sequence of Mason Pfizer Monkey Virus: An Immunosuppressive D-Type Retrovirus, Cell, vol. 45, May 1986, pp. 375–385.

Reference Raschke et al., Functional Macrophage Cell Lines Transformed by Abelson Leukemia Virus, Cell, vol. 15, Sept. 1978, pp. 261–267.

Reference Waneck et al., Abelson Leukemia Virus Induces Lymphoid and Erythroid Colonies in Infected Fetal Cell Cultures, Cell, vol. 26, Oct. 1981, pp. 79–89.

Reference Sklar et al., Transplantation and preliminary characterization of lymphoctye surface markers of Abelso virus-induced lymphomas, Nature, vol. 253, Feb. 1975, pp. 550–552.

Reference Premkumar et al., Synthesis, Surface Deposition, and Secretion of Immunoglobulins by Abelson Virus-Transformed Lymphosarcome Cell Lines, Cell, vol. 6, Oct. 1975, pp. 149–159.

Reference Risser et al., Abelson Virus-Induced Lymphomagenisis in Mice, J. Exp. Med., vol. 148, 1978, pp. 714–726.

Reference Hayward et al., Activation of a cellularonc gene by promoter insertion in ALV-induced lymphoid leukosis, Nature, vol. 290, Apr. 1981, pp. 475–480.

Reference Payne et al., Multiple arrangements of viral DNA and an activated host oncogene in bursal lymphomas, Nature, vol. 295, Jan. 1982, pp. 209–214.

Reference Shay, J. W., The Biology of Cell Fusion in *Human Hybridomas and Monoclonal Antibodies*, Eds. Engleman et al., Plenum Press, New York and London, 1985, pp. 5–12.

Reference Roder et al., The Epstein-Barr Virus-Hybridoma Technique in *Human Hybridomas and Monoclonal Antibodies*, Eds. Engleman et al., Plenum Press, N.Y. and London, 1985, pp. 55–56.

Reference Chem and Temin, Substituion of 5' Helper Virus Sequences into Non-rel Portion of Reticuloendotheliosis Virus Strain T Suppresses Transformation of Chicken Spleen Cells, *Cell*, vol. 31, Nov. 1982, pp. 111–120.

Reference Thompson et al., The efficient production of stable, human monoclonal antibody-secreting hybridomas from EBV-transformed lymphocytes using the mouse myeloma X63-Ag8.653 as a fusion partner, *Immunol. Meth.*, vol. 94, 1986, pp. 7–12.

Reference Benner et al., Immunoglobulin isotype as expression, *Eur. J. Immunol.*, vol. 11, 1981, 799–804.

(List continued on next page.)

OTHER PUBLICATIONS

Reference Romagnani et al., Activation through CD3 molecule leads a number of human T cell clones to induce IgE synthesis in vitro by B cells from allergic and nonallergic individuals, *J. Immunol.*, vol. 138, Mar. 1987, pp. 1744–1749.

Reference Romagnani et al., In vitro IgE synthesis induced by human T cell clones in normal B cells and its supression by heterogenous T cell populations, *Int. Archs Allergy appl. Immunl*, vol. 82, 1987, pp. 411–413.

Reference Del Prete et al., Human T cell clones can induce in vitro IgE synthesis in normal B cells regardless of alloantigen recognition or specificity for peculiar antigens, *Immunol.*, vol. 16, 1986, pp. 1509–1514.

Reference Seigneurin et al., Polyspecific natural antibodies and autoantibodies secreted by human lymphocytes immortalized with Epstein–Barr virus, *Blood*, vol. 71, 1988, pp. 581–585.

Reference Chen et al., Rearrangements of chicken immunoglobin genes in lymphoid cells transformed by the avian retroviral oncogene v-rel, *Proc. Natl. Acad. Sci. USA*, vol. 85, 1988, pp. 549–553.

Reference Barth and Humphries, A nonimmunosuppressive helper virus allows high efficiency induction of B cell lymphomas by reticuloendotheliosis virus strain, *J. Exp. Med.*, vol. 167, Jan. 1988, pp. 89–108.

Dialog Search Report (abstracts only).

Dialog Search Report.

International Search Report, PCT/US 88/04680, May 19, 1989.

AVIAN IMMUNOGLOBULIN-PRODUCING CELL LINES

The government may have certain rights in the invention pursuant to grant No. CA 41450 from the National Institutes of Health.

This is a continuation-in-part of U.S. patent application Ser. No. 07/289,599, filed Dec. 21, 1988, now U.S. Pat. No. 5,028,540 which is a continuation-in-part of U.S. patent application Ser. No. 07/140,263 filed Dec. 31, 1987, now U.S. Pat. No. 5,049,502.

BACKGROUND OF THE INVENTION

1. Field of the Invention

This invention relates generally to efficient in vivo and in vitro production of immunoglobulin-producing avian cell lines. More particularly, this invention concerns a method of transforming chicken B-lymphocytes using a reticuloendotheliosis virus or a v-rel gene with subsequent proliferation of B-lymphocytes that produce immunoglobulins with high efficiency.

2. Description of Related Art

Reticuloendotheliosis viruses (REVs) are a group of avian retroviruses that infect chickens, turkeys and ducks (1). The prototype virus of this group is reticuloendotheliosis virus strain T (REV-T). REV-T is highly oncogenic and causes peripheral nerve lesions and visceral reticuloendotheliosis in susceptible birds (2). The tumors caused by the infection develop rapidly, appear to be polyclonal and apparently require the expression of the v-rel oncogene carried by REV-T (3, 4).

Although the REV-T virus transforms appropriate target cells, it is replication defective and requires a helper virus for its propagation. REV-A is one example of a so-called non-(replication) defective helper virus. Such helpers are distinguished from REV-T by their ability to replicate in vitro in fibroblasts and their inability to induce acute neoplastic disease n vivo (5, 6). However, some of the helper viruses, chick syncytial virus (CSV) and REV-A, for example, independently induce a bursal-dependent B-cell lymphoma that is indistinguishable from avian leukosis virus (ALV)-induced lymphoid leukosis (6, 7). ALV and CSV are genetically unrelated but function similarly in exhibiting similar interactions with the same host oncogene in B lymphomas. These lymphomas are characterized by long latency periods, are monoclonal, and have a proviral integration of a promoter-enhancer sequence near the proto-oncogene c-myc in a susceptible cell (8, 9).

Despite numerous studies on avian cells transformed by REV-T, the identification of the target cells for the virus has not been clarified. In vitro transformed cell lines developed after infection of isolated spleen cells with REV-T(REV-A) appeared to have characteristics of immature B-lymphocytes (2, 10, 11) but the absence of specific markers that define this phenotype have prevented conclusive identification. The principal target cells transformed by REV-T(REV-A) both in vivo and in vitro have generally been believed not only to be extremely immature lymphoid cells of B-line lineage but also to fail to synthesize immunoglobulin molecules (12). Rare exceptions have been reported, but efficiency of IgM production was very low and no transformed cell was observed to synthesize detectable levels of IgG or IgA (11).

Nevertheless, a method of efficient production of antibody-producing cell clones would be useful for a variety of purposes. These include models for the study of cellular and genetic mechanisms involved in leukemogenesis, hematopoietic cell differentiation and monoclonal antibody production. Additionally, the development of monoclonals isolated from chicken antibody cell lines would offer several particular advantages. First, the chicken is more phylogenetically distinct from man than the commonly used mouse, so that chicken monoclonals could be developed against important human antigens more easily than mouse monoclonals against such antigens. Second, the allotypic heterosera traditionally used to recognize mouse antigens are weak and difficult to produce, but could be conveniently and easily recognized by chicken monoclonals; third, the epitopes generated by the chicken during infection with defined pathogens could be useful in developing effective vaccine strategies; and fourth, in many cases tumor specific antigens found on avian tumors should be recognized by the chicken, leading to understanding of tumor regression in several avian systems.

Therefore, identification of the target cells for v-rel-induced tumors and development of methods of efficient antibody production from avian cell clones would be useful not only for the reasons cited but also in developing analogous strategies in the in vivo and n vitro production of monoclonal antibody producing clones from other types of cell lines.

SUMMARY OF THE INVENTION

The present invention relates to a method for preparing antibody-producing avian cell clones. This method generally comprises: immunizing a first bird with a desired antigen; separating a population of antibody-producing B-lymphocytes from the first bird and treating the antibody-producing B-lymphocyte population with v-rel under conditions inducing transformation. To develop antibody-producing clones in vivo, the treated B-lymphocytes are transplanted into a second bird, the second bird having been pretreated to remove normal B-lymphocytes; the transformed B-lymphocytes are allowed to proliferate in the second bird; and then isolated.

To develop antibody-producing clones in vitro, the treated B-lymphocytes are not transplanted into a second bird as is done for in vivo preparation of avian cell clones. Instead, the treated B-lymphocytes are incubated under conditions that facilitate proliferation of the antibody-producing clones.

A first step in practicing the invention is the immunization of a bird with an antigen. Although the method is illustrated with a chicken, its application should include related species such as ducks and turkeys, that is, generally speaking those birds susceptible to infections by Rev-T viruses. The bird immunized should be relatively young, about six to eight weeks of age, so that Ig positive cells are readily produced. Older birds do not respond so readily to specific antigens, most likely because they have previously been exposed to a variety of antigens from the environment. The immunization may be with a variety of antigens including $TGF_\alpha$, IL-2 receptor, BSA-coupled to c-myc, insulin and the other conserved molecules.

After a bird is immunized, the immunization may be monitored by routine serological analysis, usually indicated by measurement of an antibody titer of greater than about 1/200. This is not to say that it is absolutely necessary to achieve this approximate titer or even to immunize since it would be possible to isolate antibody producing cells without antigen challenge, especially in older birds. However, without immunization, only low amounts of B-lymphocytes would be isolated.

Separation of antibody-producing lymphocytes is the next step (13). Separation of a population of B-lymphocytes from a bird is preferably from the bursa or spleen, but may also be obtained from bone marrow, gland of Harder, intestinal lining or peripheral blood of the bird. The cells may be separated from other cells and debris by standard density gradient centrifugation, for example, sucrose density gradient. Generally, the majority of antibody-producing B-lymphocytes are IgM+, at least those from the spleen and bursa, but other isotypes may be present, for example, IgG or IgA, depending on the antigen used for the immunization. In order to develop IgG or IgA clones, the separating step could, for example, utilize panning the antibody-producing B-lymphocytes on a solid surface comprising bound antibodies having binding specificity for avian IgM, IgG or IgA.

In a next step after isolation of antibody-producing B-lymphocytes from a live bird, the B-lymphocytes are treated with v-rel under conditions inducing transformation. This may involve transfection with or electroporation-induced entry of an agent containing a v-rel gene. These techniques are well known to those skilled in the art. Agents may include, for example, plasmid vectors comprising cloned v-rel. Also viruses which comprise the v-rel oncogene may be used, for example a reticuloendotheliosis virus or a reticuloendotheliosis virus and a helper virus. In a preferred practice, the helper-free reticuloendotheliosis virus is REV-T and the reticuloendotheliosis virus with a helper virus is REV-T(CSV). Other helper viruses may be used, including but not limited to spleen necrosis virus (SNV), attenuated REV-A or duck infectious anemia virus (DIAV). It has been discovered that when a virus is used to infect separated B-cells, either the virus or virus and helper virus may be used for infection. If the infected cells are then to be transferred into a second live bird, any helper virus used must be nontoxic to target cells in the second bird. Thus, REV-A, for example, appears to be directly or indirectly toxic to the target cells of the live animal; however, if the separated B-lymphocytes are transformed and subsequently propagated in vitro, cytotoxicity of the helper virus is not a concern and any suitable helper virus may be used.

After transformation in vitro of isolated B-lymphocytes, the treated B-lymphocytes may either be transferred into a second bird or proliferated in vitro in order to establish antibody producing cell lines.

It was a surprising finding that in vitro proliferation of treated B-lymphocytes was highly efficient when the cells were incubated in liquid growth medium rather than soft agar, as was the customary method of isolating and propagating these cells. Instead, it has been found that a preferred embodiment is to plate transformed B-lymphocytes in liquid medium at concentrations of infected cells that produce single infections per well. In a most preferred embodiment, the liquid growth media comprises Hahn's medium.

During n vitro proliferation, the cells may, in a preferred additional step, be treated with a desired antigen. This step is not necessary, as the bird from which the B-lymphocytes were isolated has generally been immunized with an antigen prior to separating a population of B-lymphocytes. The additional treatment with antigen, however, may induce resting antigen-specific B-cells to enter the cell cycle due to the mitogenic effect of ligand-receptor interaction and its postulated stimulation of proliferation. The cells may also or in the alternative be incubated with B-cell mitogens of which examples are one or more of lectins, cytokines and antibodies directed against B-lymphocyte surface proteins.

Rather than proliferation of antibody-producing clones in vitro, an in vivo method may be used. In this method, B-lymphocytes which have been isolated from a first bird and treated n vitro to produce transformed B-lymphocytes are transplanted into a second bird, the bird preferably being a chicken between about one week and sixteen weeks of age. Prior to transplantation, the second bird is pretreated with an agent that destroys normal B-lymphocytes, for example, cyclophosphamide. The transplanted B-lymphocytes are generally allowed to proliferate for at least about two to three days in the second bird before the cells are re-isolated.

Once in vivo proliferation in the second bird has proceeded, the B-lymphocytes are isolated from the spleen, bursa, bone marrow, liver or peripheral blood of the second bird. Isolation may be accomplished by plating out the isolated B-lymphocytes, for example in microtiter plates. The cell culturing preferably is performed in microtiter plates for a period of at least about one week. Cell clones producing antibody directed against the desired antigen are then selected.

The isolating step may involve plating out said transformed B-lymphocytes and/or selecting cell clones producing antibody directed against the desired antigen. The isolating step may also involve panning said transformed B-lymphocytes on a solid surface comprising bound antibodies having binding specificity for the avian antibody being produced or its isotype.

The population of antibody-producing B-lymphocytes are usually separated from the bursa or spleen of the first bird. The isolation step is defined further as preferably involving cells from the spleen, bursa or peripheral blood of the second bird.

For purposes of practicing the method of the present invention, the v-rel gene is recognized as the transforming agent. Since the v-rel oncogene is part of a reticuloendotheliosis virus, infection with REV-T viruses will operate to transform target cells, although transfection methods such as electroporation not involving virus may also be used to transform B-lymphocytes.

In the general practice of the present invention, the birds are preferably chickens from which immunoglobulin-producing chicken cell clones are obtained.

DESCRIPTION OF THE PREFERRED EMBODIMENT

Figure 1A:
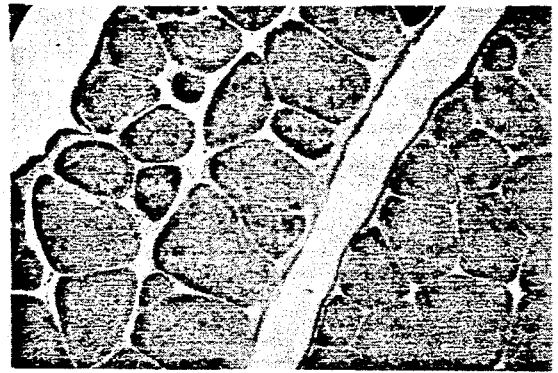
FIG. 1 shows a comparison of normal, REV-A, and CSV-infected bursal tissues. Bursal tissue from 2 week old normal, REV-A, and CSV-infected chicks was fixed in 10% neutral buffered formalin and processed for histological examination. Paraffin blocks were sectioned, at 5 μm and slides were stained with hematoxylin-eosin (A, B, and C). Bursal tissue from 4 week old chicks was snap-frozen in 2-methylbutane at −70° C. and sectioned at 8 μm. Slides were stained to reveal IgM expression using the PAP assay (D, E, and F). A and D) Normal bursa, B and E) REV-A-infected bursa, C and F) CSV-infected bursa.
Figure 1B:
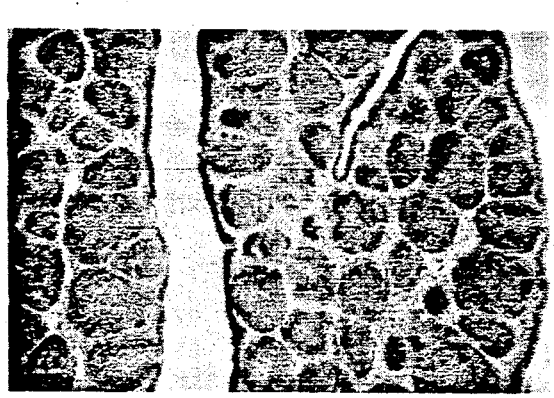

The present invention involves a method for preparing antibody-producing chicken cell clones. This method comprises a series of steps including initially immunizing a first chicken with a desired antigen. A population of antibody-producing lymphocytes from the bursa or spleen of the first chicken is separated, preferably by centrifugation in a density gradient comprising a polysaccharide such as FICOLL (Pharmacia). Additionally, in order to separate different antibody-producers, the purification may involve binding of specific lymphocyte populations by employment of specific monoclonal antibodies in a panning procedure.

The first chicken is preferably between about six and eight weeks of age. The immunization status of the first chicken is determined by routine serological analysis, for example, by measurement of an antibody titer of greater than about 1/200. The separated antibody-producing lymphocyte population is then infected with either helper-free reticuloendotheliosis virus [REV-T] or reticuloendotheliosis virus and helper virus, preferably chick syncytial virus CSV (designated REV-T(CSV)), and, when in vivo proliferation is desired, transplanted into a second chicken approximately six to eight weeks of age, the second chicken having been pretreated to remove normal B cells.

The second chicken is pretreated with cyclophosphamide to remove normal B cells prior to being transplanted with v-rel transfected or infected B-lymphocytes from the first bird. The transplanted cells are allowed to proliferate, preferably for at least two weeks. Lymphocytes from spleen, bursa or peripheral blood of the second chicken are then isolated, plated out and cultured in microtiter plates for a period of at least one week. Cell clones producing antibody such as IgG, IgA or IgM directed against the desired antigen are then selected.

Cells and Viruses

SC chicken embryo fibroblasts (CEF) were cultured in plastic dishes (Nunc, Denmark) in $ET_{10}Ca_{10}$ [Dulbecco's modified Eagle's medium (DMEM, Flow Laboratories, McLeon, Va.) containing 10% tryptose phosphate broth and 10% calf serum (Hazelton, Lenexa, Kans.) with antibiotics].

REV-A was rescued by calcium phosphate transfection of CEF with pSW253 provided by Dr. H. Temin (4). Transfected cells were cultured and transferred twice. Medium was harvested at 3 hour intervals from confluent plates, clarified by centrifugation at 250×g, passed through a 0.2 μm Nalgene filter, and stored at −70° C.

CSV(CN19691)-infected line 0 cells were provided by Dr. R. L. Witter. Culture medium from these cells was used to infect SC CEF. CSV stocks were prepared as described for REV-A.

ALV stocks were provided by Dr. Lyman Crittenden of the Regional Poultry Research Laboratories in East Lansing, Mich.

A REV-T nonproducer cell line developed in the laboratory of Dr. H. Bose by in vitro infection of spleen cells (11) was grown in $ET_{10}Ca_{10}Ck_2$ [$ET_{10}Ca_{10}$ plus 2% chick serum (GIBCO, Grand Island, N.Y.)]. Stocks of REV-T(CSV) were made by infecting the REV-T nonproducer line with CSV and harvesting virus as above after several cell transfers.

REV-T(REV-A) was harvested from a clone of the bone marrow cell line isolated in the laboratory of Dr. H. Bose (14).

The REV-T(REV-A) described herein can be obtained from the American Type Culture Collection as ATCC VR-770 (strain T).

The REV-A described herein can be obtained from REV-T(REV-A) by end-point dilution to isolate infectious REV-A free of REV-T using techniques known to one skilled in the art and as described (15).

The CSV described herein can be obtained from the American Type Culture Collection as ATCC VR-588 (strain 9437).

The REV-T(CSV) described herein can be prepared by using REV-T(REV-A) to isolate a non-producer REV-T-transformed chicken cell line using techniques known to one skilled in the art and as described (11). The isolated non-producer REV-T-transformed cell line is then infected with CSV to produce cells that release REV-T(CSV).

Chickens and Virus Infections

Embryonated SC eggs were purchased from Hyline International Hatcheries, West Des Moines, Iowa and incubated with humidity at 39° C. On day 1 after hatch, chicks were infected via intrajugular injection with $10^5$ IU of REV-A, CSV, or REV-T per bird. The chicks were housed by the Animal Resource Center, University of Texas Health Science Center at Dallas, in rooms isolated from control or avian leukosis virus-infected chicks. CSV and REV-A-infected chicks were housed in separate cages in the same isolation unit. Food and water were provided ad lib. For repopulation studies, recipient chicks were injected intraperitoneally with 3 mg Cytoxan (cyclophosphamide, Mead Johnson, Syracuse, N.Y.) daily for 4 days after hatching to eliminate the resident B-cells (16). On the sixth day post hatch, sibling donor chicks were sacrificed by cervical displacement and their bursae were surgically removed. Bursae were then rinsed in DMEM plus antibiotics and minced with scissors. A single cell suspension which was >95% positive for Ig expression was prepared from bursal pieces and washed once with medium before resuspension in 2 ml of REV-T(CSV) per $5\times10^7$ cells (moi of 0.05 for REV-T). Cells were incubated with virus for 15 min on ice followed by 45 min at 37° C. to permit virus absorption and penetration. After one wash with medium, $5\times10^6$ of the infected bursal cells were injected via the jugular vein into cytoxan-treated recipients.

Sample Collection

Hematocrit samples were obtained from the wing vein and plasma was collected from the jugular vein and prepared as previously described (17). After sacrifice, the bursa, spleen, liver, and heart were excised and weighed as whole organs. The uppermost bilateral lobes of the kidney and 7 lobes of the thymus were excised for weighing in lieu of the total organs since complete recovery of these organs is difficult and prone to error. After the organs were weighed, samples for histology were fixed in 10% neutral buffered formalin and samples for immunohistochemistry were snap-frozen in 2-methylbutane at −70° C.

Cell Line Isolation

Cell lines were isolated by preparing single cell suspensions from nodules in the liver and random sections of tissue from the spleen, thymus, and bursa. These suspensions were diluted into Hahn's medium (18) and cultured at 37° C. with 10% $CO_2$ for 48 hrs before transferring cultures at a 1:5 dilution into $ET_{10}Ca_{10}Ck_2$. Spleen and liver cultures were transferred at a 1:10 dilution every 24 to 48 hours thereafter. Bursa and thymus cultures required more time before the initial transfer; however, after the second or third transfer, these lines also required daily transfer. Liver suspensions were tested at the initial isolation for IgM expression by immunofluorescence, and all lines were assayed by the fourth or fifth transfer. Cellular DNA was isolated by the sixth cell transfer.

Virus Titrations

REV-A and CSV stocks were titrated by endpoint dilution onto SC CEF cultures as described previously (17). The REV-A titer was $2\times10^6$ IU/ml and the CSV titer was $1.5\times10^6$ IU/ml. The titer of infectious REV-T relative to the infectious titer of REV-A or CSV was determined by comparing the amount of REV-T RNA with that of the helper virus. Viral RNAs were measured by hybridization to $^{32}$P-pKW101 (v-rel) and $^{32}$P-pSW253 (REV-A). Specific activities and the size of the probes were taken into consideration. In the REV-T(REV-A) stock, the titer of REV-A was $1.5\times10^4$ IU/ml, while the relative titer of REV-T was $8\times10^4$ IU/ml. In the REV-T(CSV) stock, the titer of CSV was $5\times10^5$ IU/ml, while the relative titer of REV-T was $1\times10^5$ IU/ml.

Infectious virus present in the plasma samples of infected chicks was also titrated by endpoint dilution onto SC CEF cultures. The reverse transcriptase reaction used in this assay has been described by Waite and Allen (19).

Immunohistochemical Analysis

Antibodies used to distinguish between REV-A and CSV infection were obtained from Dr. R. L. Witter (20). The REV-A specific monoclonal antibody, 11C100, was used at a final dilution of 1:400, whereas the monoclonal antibody capable of detecting both REV-A and CSV, 11A25, was used at a final dilution of 1:200. Monoclonal antibodies Hy-19 and Hy-16, which detect chicken IgM heavy chain and chicken IgG, respectively, were developed in this laboratory.

Cells used in indirect immunofluorescence assays were washed twice in 10 mM phosphate buffer, 150 mM NaCl, pH 7.5 (PBS) and resuspended to approximately $10^6$ cells/ml. To prepare cytospins, $10^5$ cells were centrifuged at $90\times g$ and were fixed briefly in acetone before adding either Hy-19 or Hy-16 as primary antibody. Slides were incubated at 4° C. overnight, washed 3 times in cold PBS, and wiped dry before adding fluorescein-labeled goat anti-mouse IgG (Kirkegaard & Perry Laboratories, Inc., Gaithersburg, Md.). After a 90 minute incubation at 4° C., slides were washed 3 times in cold PBS, mounted in buffered glycerol, and examined by fluorescence microscopy. Frozen tissue was embedded in OCT medium (Lab-Tek Products, Naperville, IL) and sectioned on a cryostat at 8 μm. Sections were dried and fixed in ice cold acetone for 5-10 minutes. Once dried, slides were stored at −20° C. until use.

Acetone-fixed frozen tissue sections were stained with Hy-19 and Hy-16 using a peroxidase anti-peroxidase (PAP) technique. Tissues were blocked with 50% FCS in PBS containing 0.2% sodium azide and an equal volume of primary antibody was added. After a 30 minute room temperature (RT) incubation, the slides were washed in 20 mM Tris, 140 mM NaCl, pH 7.5 (TBS) 3 times for 5 minutes each at RT. After a brief fixation in 10% neutral buffered formalin, rabbit anti-mouse antibody (Dakopatts, Santa Barbara, Calif.) was added for a 20 minute incubation. After 3 TBS washes, monoclonal mouse PAP (Dakopatts) was added for another 20 minutes. After 3 TBS washes, the slides were developed in 3% ammonium acetate, pH 5.5 containing 450 μg/ml diaminobenzidine (Sigma, St. Louis, Mo.) and 0.0045% $H_2O_2$. Slides were dried, mounted, and examined by light microscopy.

Histology

Formalin-fixed samples were embedded in paraffin for histological examination and sectioned on a microtome at 5 μm. Transformed follicles were identified as described previously (21) except that bursae were serially sectioned at 200 82 m intervals throughout the entire organ and stained with methyl green pyronin (Sigma) under conditions specified by the manufacturer. Hematoxylin-eosin staining was provided by the University of Texas Southwest Medical Center Pathology Laboratory.

Analysis of Cellular DNA

Cellular DNA was prepared from red blood cells or cultured cell lines derived from tumors as previously described (17). Eco RI and Bgl II enzymes were purchased from Boehringer Mannheim, Indianapolis, Ind. Digestion conditions were as specified by the manufacturer. Analysis of DNA by Southern transfer and hybridization conditions have been previously described (17). pBB12, a plasmid containing a 1300 bp fragment of gag sequences derived from the Schmidt-Ruppin A strain of avian sarcoma virus (22) was utilized to locate endogenous viral sequences. pKW101, a plasmid containing the 967 bp Eco RI fragment of v-rel sequences (23) was provided by Dr. H. Temin and utilized to locate REV-T-specific integration sites and c-rel sequences.

The present invention relates to the following results involving the earlier-described materials and methods.

EXAMPLE 1

Rev-A and CSV Infection in the SC Chick

One day old SC chicks were infected with $10^5$ IU of either REV-A or CSV. Hematocrits, organs and plasmas were collected from chicks at 1, 2, and 4 weeks after infection to examine the progression of disease. A comparison of total body weights indicated that REV-A-infected chicks were runted relative to control chicks. The comparative data are shown in Table I.

TABLE I

| Time[a] | Birds[b] | Body Wt | Spleen | Liver | Bursa | Kidney | Heart | Thymus | Hematocrit |
|---|---|---|---|---|---|---|---|---|---|
| Uninfected | | | | | | | | | |
| 1 wk | | 13 | 58 g | 0.08% | 3.5% | 0.33% | 0.31% | 0.81% | ND[c]37.5% |
| 2 wk | 9 | 103 g | 0.12% | 2.8% | 0.60% | 0.31% | 0.79% | ND | 33.4% |
| 4 wk | 7 | 241 g | 0.20% | 2.4% | 0.80% | 0.34% | 0.67% | 0.25% | 33.7% |
| REV-A-infected | | | | | | | | | |
| 1 wk | 5 | 54 g | 0.17% | 5.0% | 0.17% | 0.30% | 0.70% | ND | 31.5% |
| 2 wk | 9 | 71 g | 0.13% | 3.7% | 0.21% | 0.30% | 0.58% | ND | 29.3% |
| 4 wk | 11 | 117 g | 0.15% | 3.9% | 0.22% | 0.29% | 0.57% | 0.15% | 18.0% |
| CSV-infected | | | | | | | | | |
| 1 wk | 4 | 64 g | 0.14% | 4.3% | 0.25% | 0.33% | 0.72% | ND | 33.5% |
| 2 wk | 10 | 94 g | 0.16% | 3.7% | 0.39% | 0.33% | 0.70% | ND | 34.3% |
| 4 wk | 7 | 187 g | 0.18% | 2.8% | 0.37% | 0.27% | 0.48% | 0.19% | 30.6% |

*SC chicks from Hyline were infected on day 1 after hatch with $10^5$ IU of REV-A or CSV via the jugular vein. Body weights are expressed as the average weight in grams. Organ weights are represented as the ratio of organ to body weight × 100. Hematocrits are averages of % packed cell volume.
[a]The time analysis was performed at 1, 2 and 4 weeks after infection as indicated.
[b]Number of birds analyzed.
[c]Not done.

While slight splenomegaly and hepatomegaly were observed, the bursa exhibited severe atrophy. By 4 weeks after infection, hematocrit values were low, indicating the presence of anemia in later stages of REV-A disease (24, 31). In contrast to REV-A infection, the consequences of CSV infection appeared relatively minor. Although atrophy of the bursa was detected, there was reduced runting and negligible anemia in the CSV-infected chick.

Figure 1C:
Figure 1D:
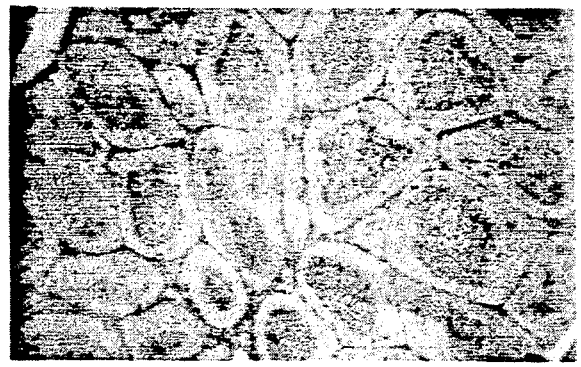
Figure 1E:
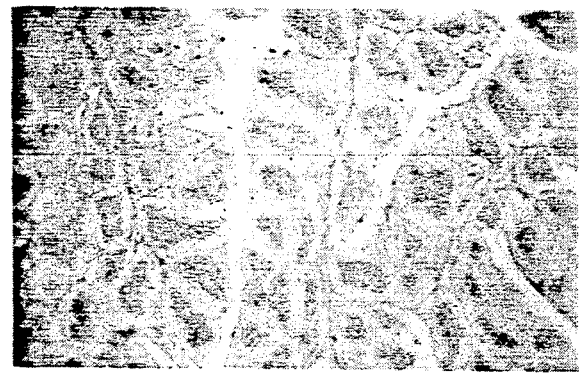
Figure 1F:

Bursae from four birds infected with either REV-A or CSV were examined at 1 and 2 weeks after infection. Hematoxylin-eosin staining of the bursal follicles revealed that a majority (>80%) of the follicles in the REV-A-infected bursa were reduced in size (FIGS. 1A and B). Expansion of the interfollicular cell mass was evident throughout the organ. The cortico-medullary boundaries of the follicles were aberrant and individual cells appeared more eosinophilic and vacuolated with chromatin condensation at the nuclear membrane. This appearance is characteristic of dead or dying cells. In contrast, only a minority (<10%) of follicles in the CSV-infected bursa were similarly affected so that the tissue as a whole appeared nearly normal (FIG. 1C). Bursae from several REV-A or CSV-infected chicks were stained to reveal IgM using the PAP assay (FIG. 1D and E). The normal bursa was characterized by even staining throughout the tissue with more intense staining in the medulla. The anti-IgM staining pattern in REV-A-infected bursae was patchy and irregular with tissue from birds sacrificed 4 weeks after infection more obviously affected. In contrast, analysis of CSV-infected tissue revealed normal distribution of IgM in the bursa (FIG. 1F).

Figure 2B:
FIG. 2 shows IgM expression in normal, REV-A, CSV, and ALV-infected splenic tissues. Spleens from 2 week old chicks were snap-frozen in 2-methylbutane at −70° C. and sectioned at 8 μm. Slides were stained to reveal IgM expression using a PAP assay. A) Normal spleen, B) REV-A-infected spleen, C) CSV-infected spleen, and D) ALV-infected spleen. Arrows mark Schweigger-Seidel sheaths and arrowheads indicate plasma cells.
Figure 2D:
Figure 2A:
Figure 2C:
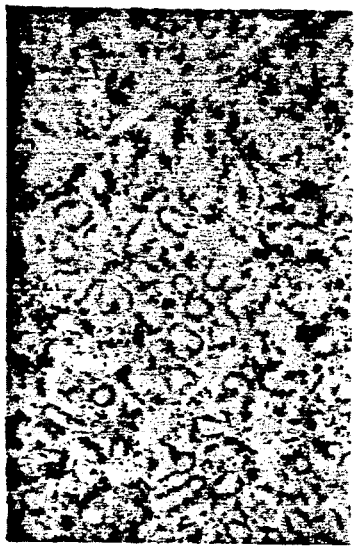

The functional integrity of the bursa was examined by determining the IgM staining pattern of the spleen. The PAP analysis was extended to splenic tissue from normal, REV-A and CSV-infected 2 week old chicks. In control spleens, the B-lymphocyte areas surrounding the Schweigger-Seidel sheaths stained positively for IgM while a few individual plasma cells stained intensely (FIG. 2A). In contrast, CSV and ALV-infected spleens contained greater numbers of intensely staining plasma cells (FIG. 2C and D). This increase in the number of plasma cells coincided with the appearance of an active immune response to virus (25, 26). Germinal centers were not observed as they require 3 to 4 weeks to develop. In distinct contrast to splenic tissue from ALV and CSV-infected chicks, REV-A-infected spleens exhibited an IgM staining pattern similar to that of uninfected birds (FIG. 2B). The absence of an increase in intensely staining plasma cells in the REV-A-infected spleen coincided with the morphological atrophy of the bursa.

The results indicated that REV-A disrupted the ability of the bursa to seed the spleen with maturing plasma cells and that this immunosuppressive effect was distinct from the induction of suppressor T-cell activity that followed REV-A infection (27) and may be related to a diminished ability of REV-A-infected chicks to mount a humoral response against T-independent antigens (28).

EXAMPLE 2

Helper Virus Replication in Bursal Lymphocytes

The amount of virus present in the plasma of REV-A and CSV-infected chicks was determined by end-point dilution. REV-A-infected birds maintained a viremia of $10^3$ to $10^4$ IU/ml of plasma throughout the 4 week time period examined, while CSV-infected chicks had 50 to 500-fold lower levels of virus circulating during the same period.

TABLE II

| VIREMIA IN REV-A AND CSV-INFECTED CHICKS* | | | |
|---|---|---|---|
| Virus | Time | Birds | Average Viremia (IU/ml) |
| REV-A | 1 wk | 5 | $1.6 \times 10^4$ |
|  | 2 wk | 9 | $1.6 \times 10^4$ |
|  | 4 wk | 4 | $1.0 \times 10^3$ |
| CSV | 1 wk | 5 | $5.0 \times 10^2$ |
|  | 2 wk | 10 | $4.0 \times 10^2$ |
|  | 4 wk | 6 | $2.5 \times 10^0$ |

*One milliliter of blook was collected from REV-A and CSV-infected chicks at 1, 2, and 4 weeks post infection in 1 ml Alsever's solution to prevent clotting. Plasma was collected aseptically after centrifugation at 800 × g to remove cellular constituents and stored at −70° C. until use. Plasma samples were assayed for virus by end-point titration on SC CEF using the assay for reverse transcriptase as an indicator of virus replication. Viremias are expressed as averages in infectious units per ml.

Figure 3A:
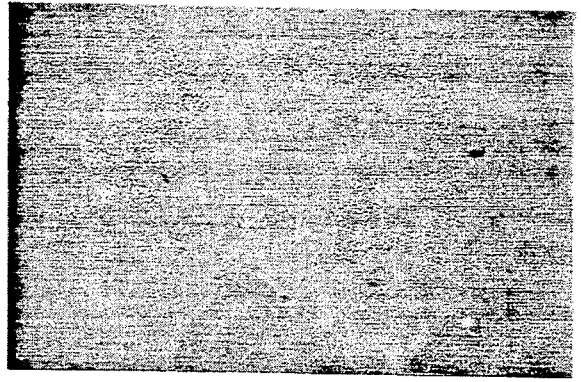
FIG. 3 shows expression of REV-A and CSV viral antigens in infected bursal tissue. Frozen sections of bursal tissue from 4 week old chicks were stained in a PAP assay with monoclonal antibody 11A25, which recognizes both REV-A and CSV antigens. A) Normal bursa, B) REV-A-infected bursa, and C) CSV-infected bursa.
Figure 3B:
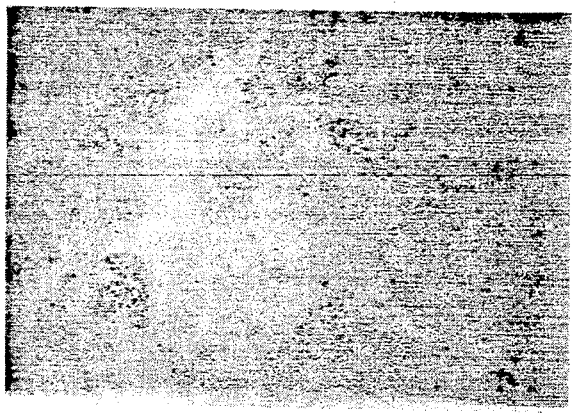
Figure 3C:
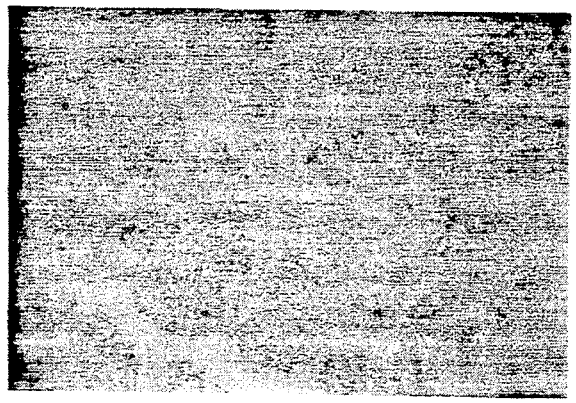

To evaluate the extent of viral infection in the bursa, monoclonal antibodies were employed to assay frozen sections of bursal tissue for the presence of viral antigens. Analysis with 11C100, specific for REV-A, detected antigen only in REV-A-infected tissue (data not shown). The analysis with 11A25, a reagent capable of reacting with both REV-A and CSV, demonstrated that both REV-A and CSV-infected tissue stained equally (FIG. 3).

Thus, despite greater levels of circulating infectious REV-A, there was no difference in the amount of viral antigen present in bursal tissue infected with either virus.

EXAMPLE 3

Viral Replication in Transformed Follicles

Figure 4:
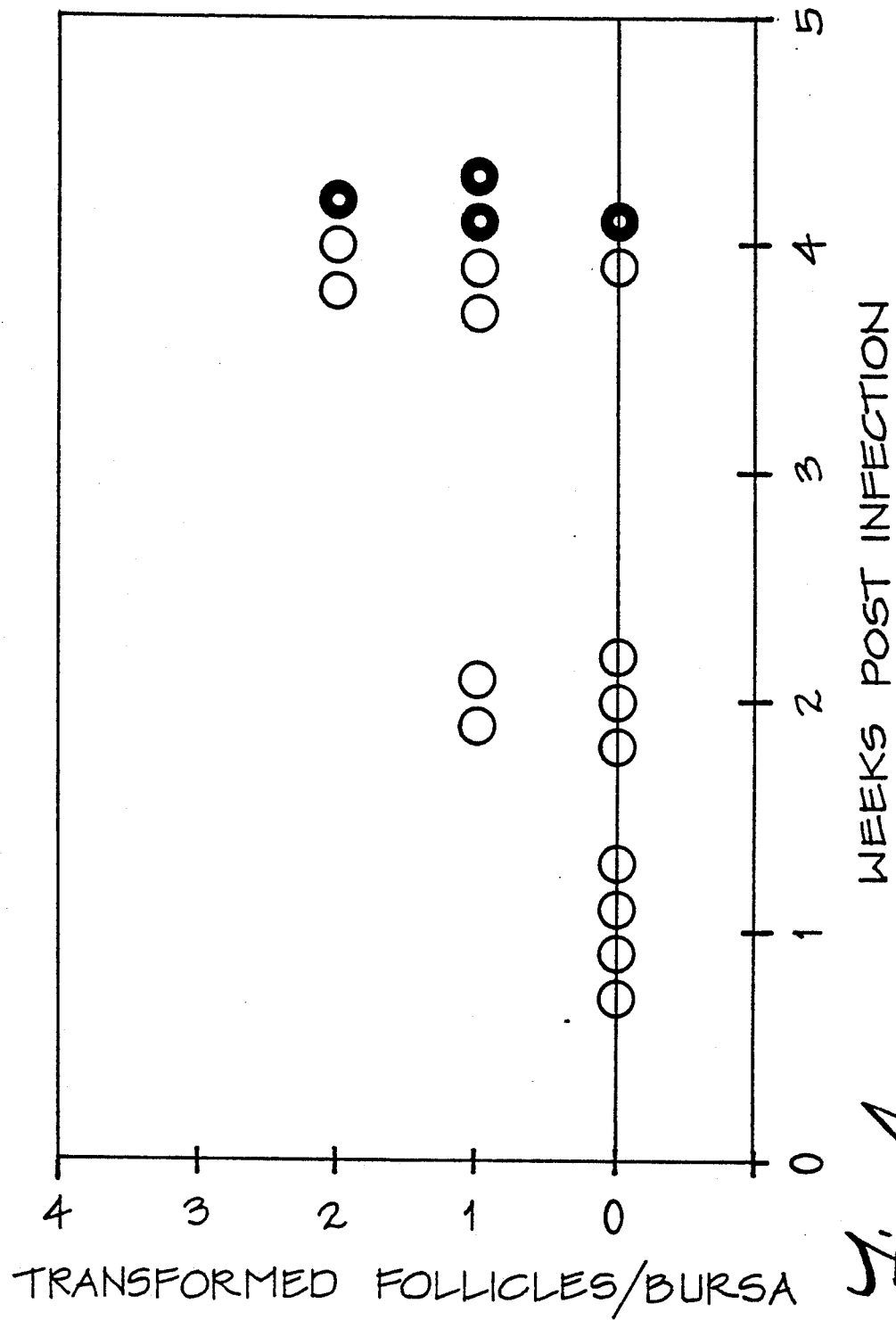
FIG. 4 shows incidence of transformed follicles in REV-A and CSV-infected chicks. SC chicks were infected with $10^5$ IU REV-A or CSV on day 1 after hatch and sacrificed at 1, 2, and 4 weeks post infection. Bursae were fixed in 10% neutral buffered formalin and processed for histological examination. Serial sections were prepared throughout the entire bursa at 200 μm intervals, stained with methyl green pyronin, and examined for the presence of transformed follicles. Each symbol represents the number of transformed follicles in a single bursa. Open symbols (0) represent CSV-infected bursae and closed symbols ( ) represent REV-A-infected bursae.
Figure 5A:
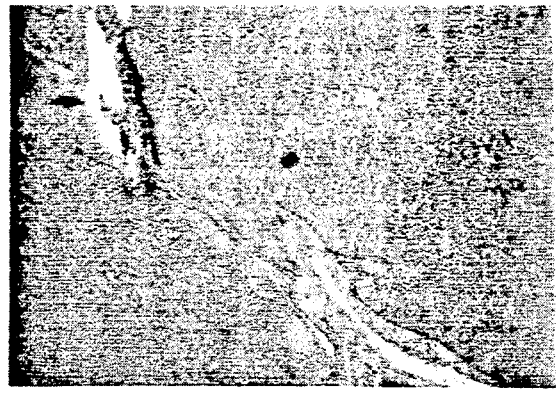
FIG. 5 shows expression of IgM in REV-T(REV-A) and REV-T(CSV)-induced tumors. Adjacent serial sections of normal, REV-T(REV-A), and REV-T(CSV)-infected livers prepared from tissue frozen at 1 week post infection were stained (i) with hematoxylin-eosin or (ii) with an anti-IgM monoclonal antibody. Hematoxylin-eosin stains of A) normal liver, B) REV-T(REV-A)-infected liver, and C) REV-T(CSV)-infected liver can be compared with PAP stains for IgM of D) normal liver, E) REV-T(REV-A)-infected liver, and F) REV-T(CSV)-infected liver. Arrows indicate non-tumor markers that allow correct orientation of the adjacent sections.
Figure 5B:
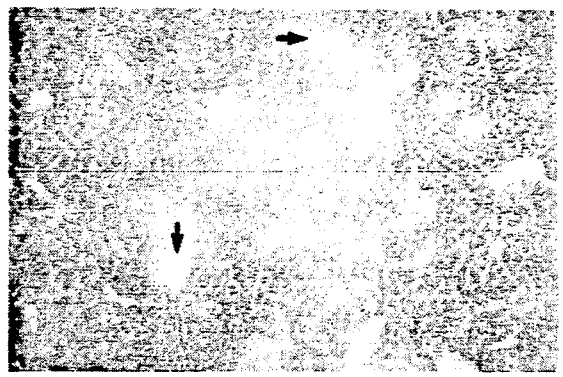
Figure 5C:
Figure 5D:
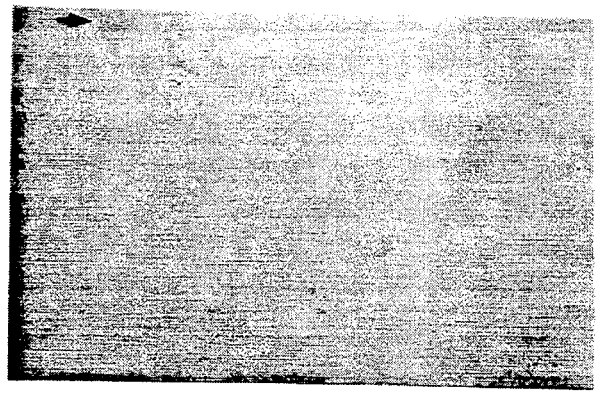
Figure 5E:
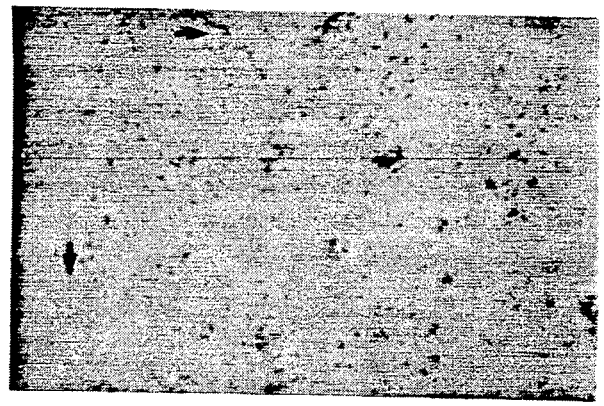
Figure 5F:
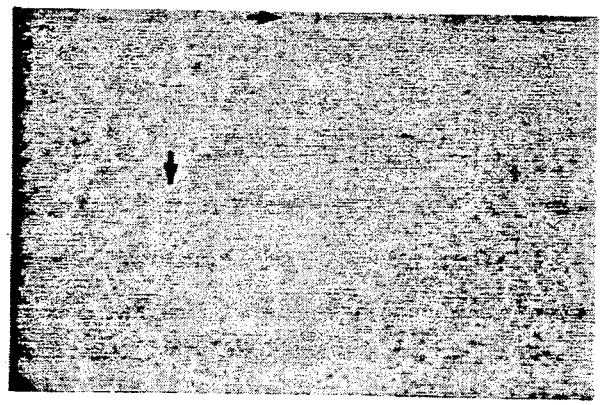

REV-A and CSV are known to cause lymphoid leukosis, a disease that is bursal-dependent and characterized by the early development of a preneoplastic lesion designated the transformed follicle (21). The presence of transformed follicles in REV-A and CSV-infected bursae was examined by serially sectioning and staining formalin-fixed bursal tissue. No more than two transformed follicles per bursa were observed in either REV-A or CSV-infected tissue (FIG. 4). Data analysis of ALV-infected chicks showed that the maximum number of transformed follicles were seen by 4 weeks after infection (21). Equivalent numbers of transformed follicles were seen in both infected tissues. This assay was repeated using frozen tissue sections and adjacent serial sections containing transformed follicles were stained by the PAP assay to detect the presence of viral antigens and IgM. Transformed follicles from both infected birds contained viral antigen, indicating that either REV-A or CSV replication can occur within proliferating bursal lymphocytes without resulting in cell death. Further, consistent with normal B-lymphocyte function, these transformed follicles exhibited IgM expression.

EXAMPLE 4

Comparison of Rev-A and CSV as Helper Viruses for Rev-T-Induced Disease

One day old SC chicks were infected with either REV-T(REV-A) or REV-T(CSV) and sacrificed at one week. Analysis of body and organ weights showed a significant increase in spleen and liver weights of birds infected with either REV-T(REV-A) or REV-T(CSV).

TABLE III

| COMPARISON OF REV-T(REV-A) AND REV-T(CSV)-INFECTED SC CHICKS* | | | | | | | | |
|---|---|---|---|---|---|---|---|---|
| Birds | Body Wt | Spleen | Liver | Bursa | Kidney | Heart | Thymus | Hematocrit |
| Uninfected | | | | | | | | |
| 13 | 58 g | 0.08% | 3.6% | 0.33% | 0.31% | 0.81% | 0.17% | 37.5% |
| REV-T(REV-A)-Infected | | | | | | | | |
| 13 | 54 g | 0.28% | 5.4% | 0.20% | 0.35% | 0.72% | 0.11% | 29.1% |
| REV-T(CSV)-Infected | | | | | | | | |
| 10 | 56 g | 1.02% | 7.2% | 0.21% | 0.39% | 0.75% | 0.13% | 29.4% |

*SC chicks from Hyline were infected with REV-T(REV-A) or REV-T(CSV) on day 1 after hatch and were sacrificed 1 week later for analysis. Samples for hematocrits were obtained from the wing vein prior to sacrifice. Body weights are represented as the average weight in grams. Organ weights are expressed as the ratio of organ to body weight × 100. Hematocrits are averages of % packed cell volume.

This increase correlated with the tumor mass observed at autopsy. Moreover, REV-T(CSV)-infected spleens were significantly larger than those from REV-T(REV-A)-infected birds. There was no difference in the bursal weights between chicks infected with either virus; however, both were decreased in comparison to uninfected controls. Anemia was observed in chicks infected with either virus, suggesting tumor involvement in the bone marrow. The large increase in the size of REV-T(CSV)-infected spleen and liver suggested that tumor development resulted from REV-T infection of a population of cells that is not present, or at least less susceptible to infection and proliferation, in the REV-T(REV-A)-infected chicks.

Spleen, liver, bursa, and thymus tissue from infected birds were analyzed for the presence of tumors. In order to detect the majority of tumors present in the affected organs, each tissue was serially sectioned in at least four distinct areas approximately 200 μm apart and examined with hematoxylin-eosin, methyl green pyronin, anti-IgM and anti-IgG staining. Six REV-T(REV-A) and four REV-T(CSV)-infected birds were analyzed. Due to the extensive range in size and number of tumors present in the affected organs, precise quantitation of the number of individual tumors per bird was difficult. However, the majority of tumors (90%) identified by hematoxylin-eosin staining in the REV-T(REV-A)-infected liver were negative for IgM expression, whereas the majority of tumors (90%) in the REV-T(CSV)-infected liver were positive for IgM expression (FIG. 5). While analysis of the spleen and bursa was more difficult due to the background of IgM positive cells in these organs, the same general observation was apparent. The number of tumors present in the thymus was too few to be informative. None of the tumors in any tissue were positive for IgG expression.

The difference between the phenotype of these two tumors was investigated by developing cell lines from tumor tissue. Twenty-seven cells lines were developed from tumors of 13 REV-T(REV-A)-infected birds and 16 cell lines were made form tumors of 9 REV-T(CSV)-infected birds. Lines derived from REV-T(REV-A)-induced tumors were never more than 30% positive for IgM expression, while lines derived from REV-T(CSV)-induced tumors were 50 to 100% positive for IgM expression (Table IV).

TABLE IV

COMPARISON OF REV-T(REV-A) AND REV-T(CSV) TUMOR-DERIVED CELL LINES*

| Phenotype | Number of REV-T(REV-A) Lines | | Number of REV-T(CSV) Lines |
|---|---|---|---|
| Uncloned | | | |
| IgM − | 17 | | 0 |
| 1-30% IgM + | 10 | | 0 |
| 50-100% IgM + | 0 | | 15 |
| Cloned | | | |
| IgM − | 34 | | 3 |
| IgM + | 0 | | 29 |
| Total Birds[a] | 13 | 9 | |
| Total Uncloned | 27 | 15 | |
| Total Cloned | 34 | 32 | |

*Tumor tissue from REV-T(REV-A) and REV-T(CSV)-infected birds were minced with scissors and cultured in Hahn's medium. Cultures were transferred at 1:5 or 1:10 dilutions 24 to 48 hours after the initial plating and passaged every 1 to 2 days thereafter. Cell lines were assayed for IgM expression after 4 or 5 transfers. Clones from these lines wre established in soft agar and analyzed for IgM expression after amplification.
[a]The number of individual birds from which uncloned cell lines were derived.

Clones from these lines were established in soft agar and analyzed for IgM and IgG expression. Of 34 REV-T(REV-A)-generated clonal lines tested, all 34 were negative for IgM expression. In contrast, of the 32 REV-T(CSV)-induced clonal lines assayed, 29 were IgM-positive. All of the clones were negative for IgG expression. The cell line analysis correlated well with the in vivo tumor analysis showing that REV-T(REV-A) infection induces primarily IgM-negative tumors while REV-T(CSV) infection induces primarily IgM-positive tumors.

EXAMPLE 5

Bursal Origin of Rev-T(CSV)-Derived IgM Positive Tumor Cell

A bursal repopulation experiment was performed which utilized the segregating endogenous viral locus 4 (EV-4) of the SC chick as a marker to differentiate between donor and recipient cells (22). EV-4-negative chicks were used as recipients while EV-4 positive chicks were employed as donors. Recipient SC chicks were treated with cytoxan and repopulated with CSV-infected donor bursal B cells. Five and a half days later, three morbid recipient birds were autopsied for the presence of tumors. For each bird, five separate tumor nodules from the liver, three separate portions of the spleen, and a portion each of bursa and thymus were removed to prepare cell suspensions for cell line development. A small sample of the liver suspension was assayed for IgM expression by immunofluorescence. In order to minimize selection, uncloned cell lines were analyzed between the 4th and 6th transfer following isolation for IgM expression, presence of EV loci, and viral integration. Analysis of the liver cell suspensions prepared at isolation showed that all samples were 50% to 100% positive for IgM. As the liver suspensions were prepared from tumor nodules and were probably clonal, the high percentage of IgM positive cells was expected. Cell lines grew out of all tissue samples taken, including the thymus preparations. When these lines were tested for IgM expression at the 4th transfer, all lines, whether derived from liver, spleen, bursa, or thymus, were greater than 99% IgM positive. This result demonstrated that IgM-positive tumor was present in all tissues and, therefore, capable of metastasis and proliferation in multiple microenvironments.

Figure 6:
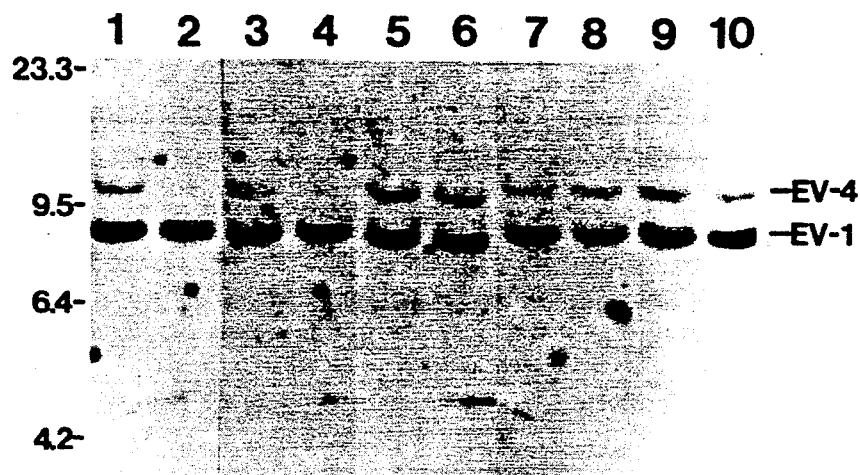
FIG. 6 shows analyses of the endogenous viral loci present in tumors isolated following transplantation of REV-T(CSV)-infected bursal lymphocytes. Cellular DNA was prepared from cell lines developed from tumors of cytoxan-treated birds repopulated with REV-T(CSV)-infected bursal lymphocytes. DNAs were digested with Eco RI and analyzed on 0.7% agarose gels, blotted to nitrocellulose, and hybridized with pBB-12 $^{32}$P-DNA in order to identify the endogenous viral loci present. Lanes 1) RBC DNA from a donor bird, 2) RBC DNA from a recipient bird, 3–10 DNAs from cell lines derived from tumors of a recipient bird. The cell lines were derived from liver nodules (lanes 3–6), bursa (lane 7), thymus (lane 8), and spleen (lanes 9 and 10). Molecular weight markers are indicated in kilobases at the left and EV loci are designated at the right. The EV-4 fragment is 10 Kb and the EV-1 is 8.7 Kb.

Because helper virus was present in REV-T(CSV), a spreading infection was established once the infected bursal cells divided following transplantation. Consequently, the DNA from the cell lines had to be analyzed for the EV-4 locus to positively identify the lines as being of donor origin. DNA samples digested with Eco RI were analyzed by Southern transfer and hybridization with pBB12 to detect EV loci. Eighteen cell lines from 2 birds were analyzed, along with donor and recipient RBC DNA. Of the 18 lines, 16 had EV-4 loci, demonstrating they were of donor cell origin (FIG. 6). This experiment demonstrated that REV-T is capable of infecting cells of bursal origin and inducing IgM positive tumors that appear at the time of tumor initiation to be both bursal-independent and capable of in vitro proliferation.

Figure 7:
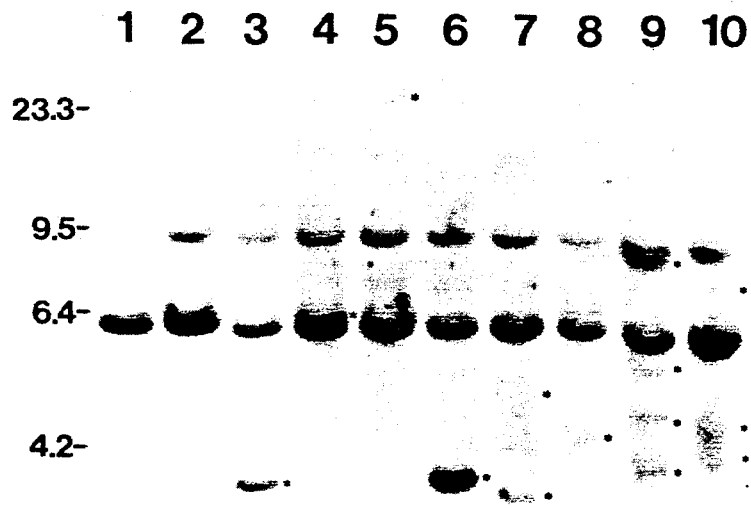
FIG. 7 shows analyses of v-rel sequences in tumors isolated following transplantation of REV-T(CSV)-infected bursal lymphocytes. Cellular DNA was prepared from cell lines developed from tumors of cytoxan-treated birds repopulated with REV-T(CSV)-infected bursal lymphocytes. DNAs were digested with Bgl II, analyzed on 0.7% agarose gels. After electrophoresis, DNA was blotted to nitrocellulose and hybridized with pKW101 $^{32}$P-DNA in order to identify the REV-T integration sites. Lanes 1) RBC DNA from a donor bird, 2) RBC DNA from a recipient bird, 3–10) DNAs from cell lines derived from tumors of a recipient bird. The cell lines were derived from liver nodules (lanes 3–6), bursa (lane 7), thymus (lane 8), and spleen (lanes 9 and 10). Molecular weight markers are indicated in kilobases at the left and REV-T specific integration sites are marked with asterisks (*). Sizes of REV-T specific integration fragments range from >23 Kb to 3.7 Kb. c-rel fragments are 15, 9, and 6 Kb and are indicated with arrowheads at the right.

The cell lines were analyzed for unique REV-T integration sites to determine whether the tumors from which these lines were developed were identical. DNA was digested with Bgl II which cuts once inside REV-T but outside v-rel sequences (29). Bgl II digestion and hybridization to v-rel, therefore, identifies a single unique fragment for each exogenous REV-T integration. The pKW101 rel-specific probe used also hybridizes to three fragments of c-rel (30). When DNA samples from the tumor lines were analyzed for rel-specific sequences, integration specific bands were detected in every line (FIG. 7). The multiple bands observed in lines developed from bursal, thymic, and splenic tumor tissue probably represent multiple, independent tumors as these cell lines were not cloned. Consistent with this interpretation, the hybridization of v-rel to the integration specific fragments is less intense than to fragments of c-rel (which served as an internal standard for a single copy gene), indicating significant heterogeneity in the tumor population. Lines developed from liver nodules had single integration-specific fragments which hybridized with intensities equivalent to that of fragments of c-rel, indicating that these lines were probably clonal with respect to REV-T integration. Twenty seven different patterns of integration were found in 29 different lines isolated from 3 birds indicating that multiple REV-T-infected bursal B-lymphocytes gave rise to tumors in this system.

EXAMPLE 6

In Vitro REV-T(CSV) Transformation of Chicken B-Cells

In vitro infection could be used directly to produce isolated clones of permanent B-cell lines secreting immunoglobulin. Cell suspensions were isolated from bursa, spleen, bone marrow and peripheral blood of 3 week old chicks. The cells were further purified by Ficoll gradient centrifugation. Preparations of these different mononuclear cells containing $10^8$ cells were infected for 30 minutes at 37° C. with approximately $1 \times 5$ infectious units of REV-T(CSV) and the cells seeded in Hahn's medium (18) in microtiter trays at $10^5$ cells per well. Four hundred wells were plated for each infected cell type including bursal, splenic, bone marrow and peripheral blood. The cells were incubated at 37° C. in $CO_2$ for seven to ten days. Wells that were positive for growth were expanded in standard growth medium as described above. In no case were more than 15% of the wells positive for growth. Each well positive for growth, therefore, could be considered in clonal in origin. These clonal outgrowths were then screened for immunoglobulin production. Forty-seven of 49 bursal clones were positive for IgM expression. Twenty-six of 40 splenic clones were positive for IgM expression. 5 of 12 bone marrow-derived clones and 3 of 9 peripheral blood-derived clones were positive for IgM expression.

Cell suspensions from bursal cells of 3-week old chicks were isolated and infected as described above with REV-T(CSV) or with REV-T(REV-A). The cells were seeded in Hahn's medium in microtiter trays in liquid growth medium at concentrations of infected cells that produced single infection events per well. Wells positive for growth were then expanded in Hahn's medium. The titer of infectious virus obtained by this method was up to $10^4$ units per ml. The clones produced were predominantly IgM positive. For infected bursal cells that were 95–99% IgM positive, the resulting clones were 99% IgM positive, while splenic cells, 25–30% IgM positive, produced clones that were 85% IgM positive. These results are shown in Table V.

TABLE V

IN VITRO TRANSFORMATION OF BURSAL AND SPLENIC MONONUCLEAR[a] CELLS BY REV-T(CSV) OR REV-T(REV-A)

| | 2 WEEK | | 4 WEEK | | 6 WEEK | |
|---|---|---|---|---|---|---|
| | Bursal | Spleen | Bursal | Spleen | Bursal | Spleen |
| REV-T(CSV) | | | | | | |
| #1 | $2 \times 10^3$ | $4 \times 10^3$ | $4 \times 10^3$ | $4 \times 10^3$ | $2 \times 10^3$ | $4 \times 10^3$ |
| #2 | ND[c] | ND | $4 \times 10^4$ | $2 \times 10^4$ | ND | ND |
| | | | (15/15) | (14/18) | | |
| REV-T(REV-A) | | | | | | |
| #1 | ND | ND | ND | ND | $2 \times 10^3$ | $2 \times 10^3$ |
| #2 | $2 \times 10^3$ | $3 \times 10^3$ | ND | $3 \times 10^3$ | $1 \times 10^3$ | ND |
| | (14/14) | (24/28) | (23/23) | (15/16) | | |

[a]Mononuclear cells were prepared from isolymph-enriched bursa or spleen.
[b]titers are given in TFU/ml. A TFU is a unit of virus which produces immortalized outgrowth of $10^5$ mononuclear cells from an individual microtiter well. All assays were done with a single preparation of virus. Each value is the average of two assays for which there was approximately 3-fold variation. Numbers in parentheses are the number of clones that stained IgM positive by immunoperoxidase.
[c]ND = not determined.

PROPHETIC EXAMPLE 7

The present example outlines the procedure contemplated by the Applicant to be useful in producing IgA or IgG REV-T(CSV) transformed chicken B-cell lines.

Production of IgA and IgG Chicken Cell Clones

A chicken is immunized with a specific antigen using intravenous administration of that antigen. Upon producing a high titer of IgA- or IgG- mediated immune reactivity, the bird is immunized a final time and sacrificed 3–5 days later. Splenic, peripheral blood and abdominal mesenteric B-lymphocytes are purified by tissue disruption or bleeding and ficoll gradient centrifugation. The B-lymphocytes are then purified by reaction with goat anti-IgG or anti-IgA and sorted for positive cells by fluorescence activated cell isolation (FACS). The sterile positive cells are concentrated and infected in vitro with REV-T (CSV) and incubated with polyclonal B-cell activators, such as lipopolysaccharide, the specific antigen and known specific B-cell mitogens. Transformed clones are isolated as usual.

Certain aspects of the present invention may be discussed specifically as follows.

High Frequency Induction of IgM Positive B-Cell Lymphomas

Results relevant to the present invention and described herein demonstrate that by using chicken syncytial virus to provide the helper functions for REV-T replication, following infection of day old chicks, the majority of induced tumors express IgM when the transfected cells are propagated in vivo prior to isolation of immunoglobulin-producing clones. The tumors within a single bird were polyclonal, which suggested that initiation and tumor development occur efficiently within a number of cells. The present results also demonstrated that bursal B-cells infected by REV-T(CSV) were able to develop as a disseminated IgM positive tumor. Dissemination to a variety of microenvironments occurred without requiring an extended period of tumor progression, indicating that the initial tumor was bursal-independent. These same tumors proliferated indefinitely as in vitro cell lines. These experiments provide the first evidence that expression of v-rel can induce IgM positive B-cell tumors with a high efficiency. Previous studies characterizing vitro-derived cell lines with a variety of heterosera, including several directed against both B and T lymphocytes of the chicken, have suggested that REV-T(REV-A) induces a poorly defined lymphoid tumor perhaps within the B-cell lineage (2, 10, 11).

The issue of tumor phenotype is somewhat confused as the original tumor was described as reticuloendothelial perhaps within the macrophage-dendritic cell lineage (31, 32, 33). Definitive markers capable of identifying these tumors and relating their phenotype to that of a normal cellular compartment have not yet been identified. In retrospect, it is significant that two REV-T-induced cell lines expressing IgM have been isolated (11, 34). In situ analysis of tumors produced following infection with REV-T(REV-A) revealed that less than 10% of these tumors expressed IgM. None of the cell lines prepared from these tumors (isolated on a completely random basis) expressed IgM. While analysis of tumor tissue has not been reported, these results are consistent with previous in vitro observations (2, 10, 11). The observations described herein that altering the helper virus that provides the viral proteins for REV-T replication also changes the type of tumor induced by v-rel expression appears to be the first report of such a phenomenon. Other helper viruses are able to influence the course of tumor development following infection by an acute transforming retrovirus but the actual type of tumor that develops remains unchanged. The development of Abelson disease can be markedly influenced by the specific helper virus with which the animal is infected but only the incidence and rate of disease onset are altered (35). Similarly, the type of Friend disease is specified by the infecting strain of SFFV, either $SFFV_a$ or $SFFV_p$, as determined by the different env regions (36). In each instance, different strains of helper MuLV can influence the course of the disease. In contrast to these examples, REV-A and CSV have a direct influence on the actual type of tumor that REV-T induces. This influence appears related to the cytotoxic effect REV-A replication has on the IgM positive B-cell population within the bursa.

REV-A Induces Extensive Bursal Atrophy

Previous work has shown that REV-A induces the appearance of a suppressor T cell that correlates with a state of immunosuppression that is independent of bursal function (27, 28, 37). While the basis for this phenomenon has not been determined, it would appear to differ from the mechanism by which REV-A influences the spectrum of REV-T-induced tumors. The IgM negative tumor induced by REV-T(REV-A) appears to result from the generalized atrophy that affects the bursa. The present analysis of the bursa demonstrates not only that the size of the bursa was reduced but also that the tissue within this organ was disrupted and the expression of IgM aberrant. It may be relevant that acute REV-A infections were known to be cytotoxic to fibroblasts in vitro (5). The interfollicular tissue, a potential source of fibroblast and stromal cell-derived growth factors, was markedly altered. While there was no direct evidence, it seemed likely that the B-cell population, which normally undergoes extensive proliferation and differentiation, had ceased division and was stationary or dying. Under these conditions, while REV-T may be able to infect the bursal lymphocyte population, activation of v-rel expression and tumor induction would be unlikely. In contrast, while the bursa in the CSV-infected chick was smaller than in the uninfected chick, both the follicular structure and the cells within the follicles appear healthy and normal. It appeared that CSV enables REV-T to induce primarily IgM-positive tumors by not destroying the bursal lymphocyte and thereby enlarging the target cell population to include proliferating, maturing B-cells.

Both viruses appeared able to replicate with equal efficiency in bursal tissue as evidenced by the expression of viral antigen. Furthermore, the expression of REV-A antigens within bursal lymphocytes did not appear to be cytotoxic by itself as transformed follicles, equally frequent in both REV-A and CSV-infected chicks, express such proteins in roughly equal quantities. It also seems unlikely that immune elimination of REV-A-infected tissue is responsible for atrophy of the bursa, since at the height of the humoral response during an ALV infection, ALV DNA sequences were eliminated rapidly from both the bone marrow and the peripheral white blood cell population while they were selectively maintained in the bursa (38). It appears likely that REV-A infection resulted in destruction of the bursal stroma such that stromal-lymphocyte interactions and/or production of essential growth factors required for B-cell proliferation and survival are absent. It is possible that one of the REV-A glycoproteins binds to bursal cells or a specific growth factor thereby blocking an interaction required for bursal lymphocyte proliferation. It has been proposed that a 26 amino acid peptide found in a number of retroviral transmembrane glycoproteins has immunosuppressive activity (39). A similar sequence has been located in gp20 for REV-A (40).

The Target Cell and V-REL-Induced Neoplastic Disease

The observation that REV-T can induce tumors that are predominantly IgM-positive demonstrates that the spectrum of cells in which v rel is able to induce neoplastic disease is larger than originally thought. While two IgM positive cell lines have been seen before, the fact that the frequency with which they can be induced is so dramatically altered in vivo by changing the helper virus illustrates that access to a given cell type plays a significant role in defining which cells are target cells for v-rel-induced tumorigenesis. While access to the IgM target cell may have been uniquely provided by the helper virus in this system, a formally similar situation has been studied with Abelson virus-induced disease. The range of cell phenotypes that can be transformed in vitro by A-MuLV includes pre-B, immature and mature B-lymphocytes, erythroid precursors, macrophages and mast cells (13, 41, 42). Not all of these cells however, serve as targets in vivo. Pre-B and immature B-lymphocytes serve as the most frequent target cells for Abelson-induced tumors (43, 44). In contrast, mast cells and macrophages serve as targets infrequently and Abelson-induced erythroid tumors have not been observed (41, 45). These data support the conclusion that a variety of factors beyond the ability of expressed v-abl sequences to function in a permissive environment are important in determining whether or not a cell serves as a target for Abelson-induced tumor development.

Defining the range of target cells has important implications for identifying the cellular genes that are involved in v-rel-mediated tumor development. The IgM positive bursal-derived tumor induced by expression of v-rel differs significantly from the IgM positive bursal derived tumor isolated following ALV infection. This ALV-induced tumor is characterized by elevated levels of c-myc resulting from viral integration within the normal cellular locus (46, 47). While these two tumors have developed from apparently similar target cells and appear phenotypically identical, their development, as outlined in Table VI, is quite distinct and indicates that significant differences exist in the genetic pathways utilized in the development of these two lymphomas.

TABLE VI

COMPARISON OF REV-T(CSV) AND ALV-DERIVED IgM POSITIVE B-CELL LYMPHOMAS

| REV-T(CSV)-Induced | ALV-Induced |
| --- | --- |
| Develop within 1-2 weeks | Development requires 3-6 months |
| Apparent single hit kinetics | Multiple hit kinetics |
| No preneoplastic lesion | Identifiable preneoplastic lesion |
| Primary tumor is bursal independent | Primary tumor is bursal dependent |
| Tumor progression not required for metastasis to non-bursal sites | Tumor progression required for metastasis to non-bursal sites |
| Adaptation to in vitro growth not required | Adaptation to in vitro growth required |

A molecular comparison of the sequences expressed in the two tumors should identify genes that function specifically in one or the other of the pathways thereby providing information that is important in dissecting the functions of v-rel and c-myc during neoplastic development in the avian B-lymphocyte.

The present invention involves the effects of both REV-A and CSV infection on bursal tissue. REV-A infection resulted in bursal atrophy, destroying both its structural and functional integrity. In contrast, the bursa in CSV-infected chicks, while reduced slightly in size, appeared both structurally and functionally normal. REV-A-induced bursal atrophy was not a result of viral replication in the B-lymphocyte as: (i) both viruses were capable of inducing, with equal efficiency, the formation of preneoplastic lesions containing proliferating B-lymphocytes; and, (ii) it appeared that equivalent amounts of viral antigen were expressed in the bursa of chicks infected with either virus.

In REV-T(REV-A)-infected chicks, the majority of tumors that developed were negative for IgM expression. In contrast the majority of tumors induced by REV-T(CSV) infection were IgM positive. This finding was confirmed by recovery of IgM negative cell lines from REV-T(REV-A)-infected chicks and IgM positive cell lines from REV-T(CSV)-infected chicks. In addition, repopulation studies showed that IgM-positive bursal-derived cells served as target cells for REV(CSV)-induced lymphomas. REV-T can induce IgM-positive B-cell lymphomas with high efficiency. Infections by the helper viruses, REV-A and CSV, differ dramatically in their effects on the composition of the population of cells that serve as targets for REV-T-induced neoplasia.

The present invention has been described in terms of particular embodiments fund by the inventors to comprise preferred modes of practice of the invention. It will be appreciated by those of skill in the art that in light of the present disclosure numerous modifications and changes can be made in the particular embodiments exemplified without departing from the intended scope of the invention. For example, the described in vitro procedure should work using any v-rel expressing virus including helper-free REV-T and REV-T packaged by other helper viruses such as DIAV, SNV or REV-A variants. The present results indicate that this procedure works even with REV-A as a helper virus, though less efficiently. This in vitro procedure should also be usable following electroporation or transfection of the v-rel gene into different lymphocyte populations. All such modifications are intended to be included within the scope of the claims.

The references listed below are incorporated herein by reference to the extent they supplement, explain, provide a background for or teach methodology, techniques and/or compositions employed herein.

REFERENCES

1. Purchase, H. G., C. Ludford, K. Nazerian, and H. W. Cox (1973). A new group of oncogenic viruses: reticulo-endotheliosis, chick syncytial, duck infectious anemia, and spleen necrosis viruses. J. Natl. Cancer Inst., 51:489.
2. Shibuya, T., I. Chen, A. Howatson, and T. W. Mak. (1982). Morphological, immunological, and biochemical analyses of chicken spleen cells transformed in vitro by reticuloendotheliosis virus strain T. Cancer Res., 42:2722.
3. Wong, T. C., and M. M. C. Lai (1981). Avian reticuloendotheliosis virus contains a new class of oncogene of turkey origin. Virology, 111:289.
4. Chen, I. S. Y., T. W. Mak, J. J. O'Rear, and H. M. Temin (1981). Characterization of reticuloendotheliosis virus strain T DNA and isolation of a novel variant of reticuloendotheliosis virus strain T by molecular cloning. J. Virol., 40:800.
5. Temin, H. M., and V. K. Kassner (1974). Replication of reticuloendotheliosis viruses in cell culture: Acute infection. J. Virol., 13:291.
6. Witter, R. L., E. J. Smith, and L. B. Crittenden (1981). Tolerance, viral shedding, and neoplasia in chickens infected with non-defective reticuloendotheliosis viruses. Avian Dis., 25:374.
7. Witter, R. L., and L. B. Crittenden (1979). Lymphomas resembling lymphoid leukosis in chickens inoculated with reticuloendotheliosis virus. Int. J. Cancer., 23:673.
8. Noori Daloii, M. R., R. A. Swift, and H-J. Kung (1981). Specific integration of REV proviruses in avian bursal lymphomas. Nature, 294:574.
9. Swift, R. A., E. Shaller, R. L. Witter, and H-J. Kung (1985). Insertional activation of c-myc by reticuloendotheliosis virus in chicken B lymphoma: Nonrandom distribution and orientation of the proviruses. J. Virol., 54:869.
10. Beug, H., H. Muller, S. Grieser, G. Doederlein, and T. Graf. (1981). Hematopoietic cells transformed in vitro by REV-T avian reticuloendotheliosis virus express characteristics of very immature lymphoid cells. Virology, 115:295.
11. Lewis, R. B., J. McClure, B. Rup, D. W. Niesel, R F. Garry, J. D. Hoelzer, K. Nazerian, and H. R. Bose (1981). Avian reticuloendotheliosis virus: Identification of the hematopoietic target cell for transformation. Cell, 25:421.
12. Zhang, J., Bargmann, W. and Bose, Jr., H. R. (1989). Rearrangement and Diversification of Immunoglobulin Ligh-Chain Genes in Lymphoid Cells Transformed by Reticuloendotheliosis Virus. Mol. and Cell. Biol., 9:4970.
13. Siden, E. J., D. Baltimore, D. Clark, and N. E. Rosenberg (1979). Immunoglobulin synthesis by lymphoid cells transformed in vitro by Abelson murine leukemia virus. Cell, 16:389.
14. Franklin, R. B., R. L. Maldonado, and H. R. Bose (1974). Isolation and characterization of reticuloendotheliosis virus transformed bone marrow cells. Intervirol., 3:342.
15. Hoelzer, J. D., R. B. Franklin, and H. R. Bose (1979). Transformation by reticuloendotheliosis virus: development of a focus assay and isolation of a nontransforming virus. Virology, 93:20.
16. Eskola, J., and P. Toivanen (1974). Effect of in vivo treatment with cyclophosphamide on lymphoid system in chicken. Cell. Immunol., 13:459.
17. Baba, T. W., and E. H. Humphries (1984). Avian leukosis virus infection: Analysis of viremia and DNA integration in susceptible and resistant chicken lines. J. Virol., 51:123.
18. Hahn, E. C., L. Ramos, and A. J. Kenyon (1977). Lymphoproliferative diseases of fowl: JM-V leukemic lymphoblasts in cell culture: brief communication. J. Natl. Cancer Inst., 59:267.
19. Waite, M. R. F., and P. T. Allen (1975). RNA-directed DNA polymerase activity of reticuloendotheliosis virus: Characterization of the endogenous and exogenous reactions. J. Virol., 16:872.
20. Cui, Z-Z., L. F. Lee, R. F. Silva, and R. L. Witter (1986). Monoclonal antibodies against avian reticuloendotheliosis virus: identification of strain-specific and strain-common epitopes. J. Immunol., 136:4237.
21. Baba, T. W., and E. H. Humphries (1985). Formation of a transformed follicle is necessary but not sufficient for development of an avian leukosis virus-induced lymphoma. Proc. Natl. Aca. Sci. (USA)., 82:213.
22. Humphries, E. H., M. L. Danhof, and Hlozanek I (1984). Characterization of endogenous viral loci in five lines of white leghorn chickens. Virology., 135:125.
23. Wilhelmsen, K. C., and H. M. Temin (1984). Structure and dimorphism of c-rel (turkey), the cellular homolog to the oncogene of reticuloendotheliosis virus strain T. J. Virol., 49:521.
24. Taylor, H. W., and L. D. Olson (1973). Chronologic study of the T-virus in chicks. II. Development of hematologic changes. Avian Dis., 17:794.
25. DeBoer, G. F., H. J. L. Maas, J. Van Vloten, and J. E. Groenendal (1981). Horizontal transmission of lymphoid leukosis virus. Influence of age, maternal antibodies and degree of contact exposure. Avian Path., 10:343.
26. Crittenden, L. B., E. J. Smith, and A. M. Fadly (1984). Influence of endogenous viral gene expression and strain of exogenous avian leukosis virus (ALV) on mortality and ALV infection and shedding in chickens. Avian Dis., 28:1037.
27. Rup, B. J., J. L. Spence, J. D. Hoelzer, R. B. Lewis, C. R. Carpenter, A. S. Rubin, and H. R. Bose (1979). Immunosuppression induced by avian reticuloendotheliosis virus: Mechanism of induction of the suppressor cell. J. Immunol., 123:1362.
28. Witter, R. L., L. F. Lee, L. D. Bacon, and E. J. Smith (1979). Depression of vaccinal immunity to Marek's disease by infection with reticuloendotheliosis virus. Infect. Immun., 26:90.
29. Rice, N. R., R. R. Hiebsch, M. A. Gonda, H. R. Bose, and R. V. Gilden (1982). Genome of reticuloendotheliosis virus: Characterization by use of cloned proviral DNA. J. Virol., 42:237.
30. Chen, I. S. Y., K. C. Wilhelmsen, and H. M. Temin (1983). Structure and expression of c-rel, the cellular homolog to the oncogene of reticuloendotheliosis virus strain T. J. Virol., 45:104.
31. Mussman, H. C., and M. J. Twiehaus (1971). Pathogenesis of reticuloendothelial virus disease in chicks—an acute runting syndrome. Avian Dis., 15:483.
32. Olson, L. D. (1967). Histopathologic and hematologic changes in moribund stages of chicks infected with T-virus. Amer. J. Vet. Res., 28:1501.
33. Theilen, G. H., R. F. Zeigel, and M. J. Twiehaus (1966). Biological studies with RE virus (strain T) that induces reticuloendotheliosis in turkeys, chickens, and Japanese quail. J. Natl. Cancer Inst., 37:731.
34. Keller, L. H., R. Rufner, and M. Sevoian (1979). Isolation and development of a reticuloendotheliosis virus-transformed lymphoblastoid cell line from chicken spleen cells. Infect. Immun., 25:694.
35. Rosenberg, N., and D. Baltimore (1978). The effect of helper virus on Abelson virus-induced transformation of lymphoid cells. J. Exp. Med., 147:1126.
36. Ruscetti, S., and L. Wolff (1985). Biological and biochemical differences between variants of spleen focus-forming virus can be localized to a region containing the 3'end of the envelope gene. J. Virol., 56:717.
37. Rup, B. J., J. D. Hoelzer, and H. R. Bose (1982). Helper viruses associated with avian acute leukemia viruses inhibit the cellular immune response. Virology, 116:61.
38. Baba, T. W., and E. H. Humphries (1986). Selective integration of avian leukosis virus in different hematopoietic tissues. Virology, 155:557.
39. Cianciolo, G. J., T. D. Copeland, S. Oroszlan, and R. Snyderman (1985). Inhibition of lymphocyte proliferation by a synthetic peptide homologous to retroviral envelope proteins. Science, 230:453.
40. Sonigo, P., C. Barker, E. Hunter, and S. Wain-Hobson (1986). Nucleotide sequence of Mason-Pfizer monkey virus: An immunosuppressive D-type retrovirus. Cell, 45:375.
41. Raschke, W. C., S. Baird, P. Ralph, and I. Nakoinz (1978). Functional macrophage cell lines transformed by Abelson leukemia virus. Cell, 15:261.
42. Waneck, G. L., and N. Rosenberg (1981). Abelson leukemia virus induces lymphoid and erythroid colonies in infected fetal cell cultures. Cell, 26:79.
43. Sklar, M. D., E. M. Shevach, I. Green, and M. Potter (1975). Transplantation and preliminary characterization of lymphocytic surface markers of Abelson virus-induced lymphomas. Nature, 253:550.
44. Premkumar, E., M. Potter, P. A. Singer, and M. D. Sklar (1975). Synthesis, surface deposition, and secretion of immunoglobulins by Abelson virus-transformed lymphosarcoma cell lines. Cell, 6:149.
45. Risser, R., M. Potter, and W. P. Rowe (1978). Abelson virus-induced lymphomagenesis in mice. J. Exp. Med., 148:714.

46. Hayward, W. S., B. G. Neel, and S. M. Astrin (1981). Activation of a cellular onc gene by promoter insertion in ALV-induced lymphoid leukosis. Nature, 290:475.
47. Payne, G. S., J. M. Bishop, and H. E. Varmus, (1982). Multiple arrangements of viral DNA and an activated host oncogene in bursal lymphomas. Nature, 295:209.

Changes may be made in the construction, operation and arrangement of the various parts, elements, steps and procedures described herein without departing from the concept and scope of the invention as defined in the following claims.

What is claimed is:

1. A method of preparing antibody-producing avian cell clones, the method comprising:
   immunizing a bird with a desired antigen;
   separating a population of antibody-producing B-lymphocytes from said bird;
   treating the B-lymphocytes in vitro with v-rel an a cytotoxic helper virus to induce cell transformation; and
   incubating said v-rel/cytotoxic helper virus treated B-lymphocytes in vitro under conditions facilitating proliferation of antibody-producing B-lymphocytes.

2. The method of claim 1 wherein the population of B-lymphocytes is separated from bursa, spleen, bone marrow, gonad of Harder, intestinal lining or peripheral blood of the bird.

3. The method of claim 1 wherein the separating involves panning said antibody-producing B-lymphocytes on solid surface comprising bound antibodies having binding specificity for avian IgM, IgG or IgA.

4. The method of claim 1 wherein the v-rel is contained within a reticuloendothelial virus.

5. The method of claim 4 wherein the reticuloendothelial virus is REV-T and wherein the cytotoxic helper virus is REV-A.

6. The method of claim 1 wherein the incubating step comprises plating the B-lymphocytes in liquid growth medium at concentrations of infected cells that produce single infections per well.

7. The method of claim 6 wherein the liquid growth media comprises Hahn's medium.

8. The method of claim 1 wherein the incubating step comprises treatment of the v-rel treated B-lymphocytes in culture medium comprising the desired antigen.

9. The method of claim 1 wherein the incubating step comprises incubation of the treated B-lymphocyte population in culture medium comprising B-cell mitogens.

10. The method of claim 9 wherein the B-cell mitogens are one or more of lectins, cytokines and antibodies directed against B-lymphocyte surface proteins.

11. The method of claim 1 wherein the bird is between about six weeks and eight weeks of age.

12. The method of claim 1 wherein the antibody produced is of an IgM isotype.

* * * * *

UNITED STATES PATENT AND TRADEMARK OFFICE
CERTIFICATE OF CORRECTION

PATENT NO. : 5,258,299
DATED : November 2, 1993
INVENTOR(S) : Eric H. Humphries

It is certified that error appears in the above-indentified patent and that said Letters Patent is hereby corrected as shown below:

Col. 23, line 22: after "v-rel" change "an" to "and"

Signed and Sealed this

Sixteenth Day of May, 1995

Attest:

BRUCE LEHMAN

*Attesting Officer*      *Commissioner of Patents and Trademarks*